US005432857A

United States Patent [19]

Geddes

[11] Patent Number: 5,432,857

[45] **Date of Patent: * Jul. 11, 1995**

[54] DUAL BANDPASS SECONDARY SOURCE

[75] Inventor: Earl R. Geddes, Livonia, Mich.

[73] Assignee: Ford Motor Company, Dearborn, Mich.

[ * ] Notice: The portion of the term of this patent subsequent to Jun. 7, 2011 has been disclaimed.

[21] Appl. No.: 204,826

[22] Filed: Mar. 2, 1994

Related U.S. Application Data

[63] Continuation of Ser. No. 862,884, Apr. 3, 1992, Pat. No. 5,319,165, which is a continuation-in-part of Ser. No. 514,624, Apr. 25, 1990, Pat. No. 5,119,902.

[51] Int. Cl.[6] .......... A61F 11/06; H03B 29/00

[52] U.S. Cl. .......... 381/71; 181/206

[58] Field of Search .......... 381/71, 94; 181/206

[56] References Cited

U.S. PATENT DOCUMENTS

| | | | |
|---|---|---|---|
| 1,969,704 | 8/1934 | D'Alton . | |
| 4,153,815 | 5/1979 | Chaplin et al. | 381/71 |
| 4,472,605 | 9/1984 | Klein . | |
| 4,473,906 | 9/1984 | Warnaka et al. | 181/206 |
| 4,480,333 | 10/1984 | Ross | 381/71 |
| 4,520,237 | 5/1985 | Murakami . | |
| 4,549,631 | 10/1985 | Bose | 181/156 |
| 4,665,549 | 5/1987 | Eriksson et al. | 381/71 |
| 4,665,550 | 5/1987 | Haas | 381/182 |
| 4,669,122 | 5/1987 | Swinbanks | 381/71 |
| 4,677,676 | 6/1987 | Eriksson | 381/71 |
| 4,677,677 | 6/1987 | Eriksson | 381/71 |
| 4,736,431 | 4/1988 | Allie et al. | 381/71 |
| 4,783,817 | 11/1988 | Hamada et al. | 381/71 |
| 4,783,820 | 11/1988 | Lyngdorf et al. | 381/89 |
| 4,805,733 | 2/1989 | Kato et al. | 181/206 |
| 4,815,139 | 3/1989 | Eriksson et al. | 381/71 |
| 4,837,834 | 6/1989 | Allie | 381/71 |
| 4,876,722 | 10/1989 | Dekker et al. | 381/71 |
| 4,878,188 | 10/1989 | Ziegler, Jr. . | |
| 4,989,254 | 1/1991 | Amalaha | 381/202 |
| 5,146,505 | 9/1992 | Pfaff et al. | 381/71 |
| 5,229,556 | 7/1993 | Geddes | 181/206 |
| 5,233,137 | 8/1993 | Geddes | 181/206 |
| 5,257,316 | 10/1993 | Takeyama et al. | 381/71 |
| 5,272,286 | 12/1993 | Cain et al. | 181/206 |

FOREIGN PATENT DOCUMENTS

| | | |
|---|---|---|
| 768373 | 8/1934 | France . |
| 2191063 | 12/1987 | United Kingdom . |

OTHER PUBLICATIONS

AES, "Bandpass Loudspeaker Enclosures", Publication Nov., 1986, 2383, pp. 1-26, Figs. 1-24.

*Primary Examiner*—Curtis Kuntz
*Assistant Examiner*—Ping W. Lee
*Attorney, Agent, or Firm*—Roger L. May; Mark L. Mollon

[57] ABSTRACT

An active muffler for use in motor vehicles comprises a sensor, an electronic control responsive to the signal generated by the sensor for producing a drive signal delivered to a transducer which emits cancellation pulses phased 180° from the sound pressure pulses passing through a conduit, where both front and rear sides of the transducer are acoustically coupled to the conduit to improve the efficiency of the transducer operation. Preferably, the acoustic coupling comprises an enclosed chamber including a port for communicating with the conduit which can be tuned to resonate at predetermined frequencies. When both sides of the transducer are so coupled to the conduit, the transducer has increased efficiency over a broad band of frequencies, and the frequency band can be broadened at the low end as required to accommodate the frequencies generated by a source of noise. A tandem transducer mounting arrangement according to the present invention reduces vibration of the housing. The system is particularly suitable for use in adapting noise cancellation techniques to replace passive mufflers on motor vehicles.

10 Claims, 2 Drawing Sheets

FIG 1
PRIOR ART
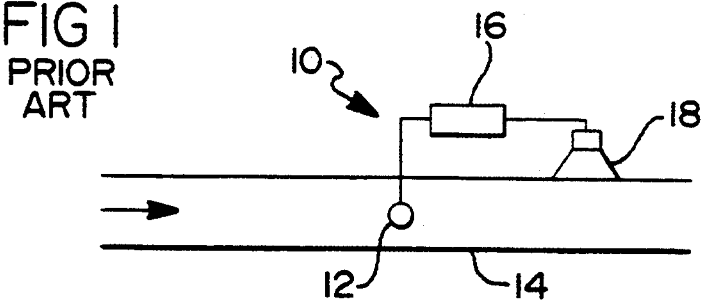
FIG 2
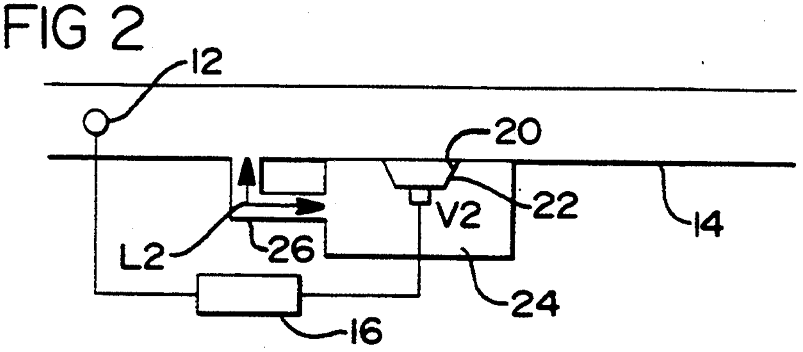
FIG 3
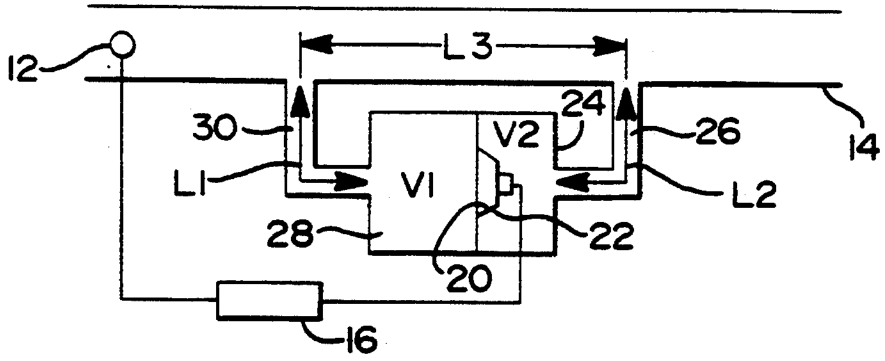
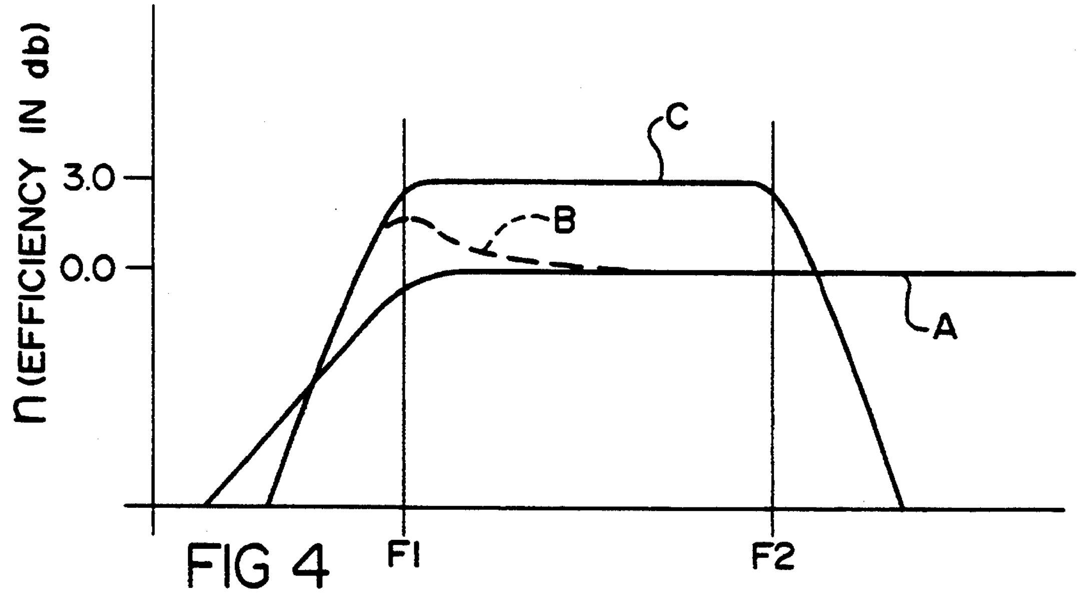
FIG 4

DUAL BANDPASS SECONDARY SOURCE

This is a continuation of U.S. application Ser. No. 07/862,884 filed on Apr. 3, 1992, now U.S. Pat. No. 5,319,165, which is a continuation-in-part of U.S. application Ser. No. 514,624 for Active Muffler Transducer Arrangement, filed Apr. 25, 1990.

TECHNICAL FIELD

The present invention relates generally to noise reduction apparatus and, more particularly, to active sound cancellation devices made applicable for use with motor vehicles.

BACKGROUND ART

Internal combustion engines typically used in motor vehicles generate a substantial amount of noise due to the combustion occurring within the engine. Conventionally, the noise generated is suppressed by a passive muffler system in which the sound waves are broken up by resonance with baffles, passageways and the like or absorbed by fibrous material. However, such techniques of reducing the sound level also obstruct the free flow of exhaust gases through the exhaust conduits and, therefore, substantially interfere with efficient operation of the vehicle's engine by interfering with the release of combustion products and inhibiting the replacement of the combusted gases with fresh fuel in the engine cylinders. Nevertheless, despite the reduction in economy and performance, the need for substantially reduced noise levels requires the use of mufflers on all production motor vehicles.

Although active noise cancellation systems have been employed with large ducts used for heating and ventilation in large buildings, the previously known systems are not well adapted for use in the environment of motor vehicles. For example, U.S. Pat. No. 4,473,906 to Warnaka et al discloses numerous prior art sound attenuation system embodiments. In general, sensed sound pressure produces a signal adapted to drive a loudspeaker for inputting cancellation signals into the duct. The cancellation signal is an acoustic pulse signal 180° out of phase with the signal passing past the speaker through the duct. The prior art embodiments also illustrate improved noise attenuation performance by reducing the effect of the feedback of the cancellation signal which arrives at the sensor. The patent discusses the inclusion of additional transducers and electronic controls to improve the performance of the active acoustic attenuator.

U.S. Pat. No. 4,677,677 to Eriksson further improves attenuation by including an adaptive filter with on-line modeling of the error path and the canceling speaker by using a recursive algorithm without dedicated off-line pretraining. U.S. Pat. No. 4,677,676 adds a low amplitude, uncorrelated random noise source to a system to improve performance. Likewise, U.S. Pat. Nos. 4,876,722 to Decker et al and 4,783,817 to Hamada et al disclose particular component locations which are performance related and do not adapt active attenuator noise control systems to motor vehicles. However, none of these improvements render the system applicable to muffle engine noise in the environment of a motor vehicle.

The patented, previously known systems often employ extremely large transducers such as 12 or 15 inch loudspeakers of conventional construction. Such components are not well adapted for packaging within the confines of the motor vehicle and, particularly, within the undercarriage of the motor vehicle. Moreover, since the lowest frequency of the signal which must be canceled is on the order of 25 hertz, it may be appreciated that a large loudspeaker is used under conventional wisdom to generate sound signals with sufficient amplitude in that range, and such speakers are not practical to mount beneath a motor vehicle. Moreover, although the highest frequencies encountered are easier to dissipate because of their smaller wavelength, the highest frequency to be canceled is on the order of 250 hertz.

Moreover, many of the prior art references teach the inclusion of such speakers within the ducts subjected to the sound pressure signal. It may be appreciated that the loudspeakers discussed above could not be installed in that manner in conventional exhaust conduits for motor vehicles. Furthermore, the harsh environmental conditions within such a chamber do not teach or suggest that such components can be employed in a motor vehicle. Moreover, while packaging considerations might suggest that the size of a speaker be reduced and compensated for by additional speakers of smaller size, such multiplication of parts substantially increases costs while reducing reliability.

Although there have been known techniques for increasing the efficiency of audio loudspeakers, those teachings have not been considered readily applicable to active noise attenuating systems. French Patent No. 768,373 to D'Alton, U.S. Pat. No. 4,549,631 to Bose, and the Bandpass Loudspeaker Enclosures publication of Geddes and Fawcett presented at the 1986 convention of the Audio Engineering Society acknowledge the phenomena of tuning loudspeaker output by the use of chambers including ports. The recognition of this phenomena has been limited to its effect upon audio reproduction and, particularly, dispersion of the audio signal to an open area outside the loud-speaker enclosure. There is no teaching or suggestion in the prior art that noise cancellation techniques are improved by such phenomena. In addition, the closed conduit system of motor vehicle exhaust systems, and the harsh environment associated with such systems, do not suggest that loudspeaker developments for use in open areas are readily applicable or practical to provide active muffler systems in motor vehicles.

SUMMARY OF THE INVENTION

The present invention substantially reduces the difficulty of employing active attenuation technology to motor vehicle exhaust systems by compensating for the effects of oppositely phased front and rear emissions from a transducer to effect cancellation of sound pressure pulses in a conduit enclosure. In general, at least one side of each of two speaker diaphragms is enclosed within a chamber including a port acoustically coupled to the conduit for cancelling sound pressure pulses in the conduit. Preferably, both sides of each transducer diaphragm are enclosed within separated chambers, each of which has a port. Preferably, each of two ported chambers is tuned for resonant frequencies at or near the high and low ends, respectively, of the cancellation signal bandwidth containing the sound pressure pulses to be canceled.

In the preferred embodiment, compensation for the reaction of the transducer mounting to the movements of the transducer can be provided by mounting a pair of transducers in a housing enclosure. The speakers are juxtaposed and preferably positioned with facing transducer diaphragm sides coaxially aligned with each other. The facing sides of the diaphragms are driven in a common chamber, while the opposite sides are in chambers ported to the exhaust conduit. With both transducers driven in phase but so that facing diaphragm sides are driven in opposite directions, vibration of the housing is reduced by the induced cancellation effect. The common chamber is preferably ported for communication with the exhaust conduit.

Thus, the present invention provides an active noise cancellation system particularly well adapted for use in motor vehicles. The increased efficiency of using both sides of the diaphragm of the transducer arrangement reduces the packaging requirements for the noise cancellation system, while the opposite but equal displacement of the two transducer diaphragms control undesirable vibration. Moreover, the mounting arrangement permits easier and protected mounting of a transducer despite the environment and high temperature conditions involved with exhaust system components. Furthermore, the tuning of ports and enclosure chambers provides a cancellation signal width particularly well adapted for use in the noise frequency range associated with conventional motor vehicle engines. Accordingly, the present invention renders active muffler systems applicable to motor vehicles in a practical way.

BRIEF DESCRIPTION OF THE DRAWINGS

The present invention will be more clearly understood by reference to the following detailed description when read in conjunction with the accompanying drawing in which like reference characters refer to like parts throughout the views and in which:

FIG. 1 is a diagrammatic view of a conventional noise attenuation system used for the ventilation ducts of buildings and the like;

FIG. 2 is a diagrammatic view similar to FIG. 1 but showing an improved transducer mounting arrangement for an active muffler in a motor vehicle;

FIG. 3 is a diagrammatic view of an active attenuation system but showing a modification of the transducer mounting;

FIG. 4 is a graphical representation of the performance of the embodiments shown in FIGS. 1–3 for the sake of comparison.

DETAILED DESCRIPTION OF THE BEST MODE

Figure 5:
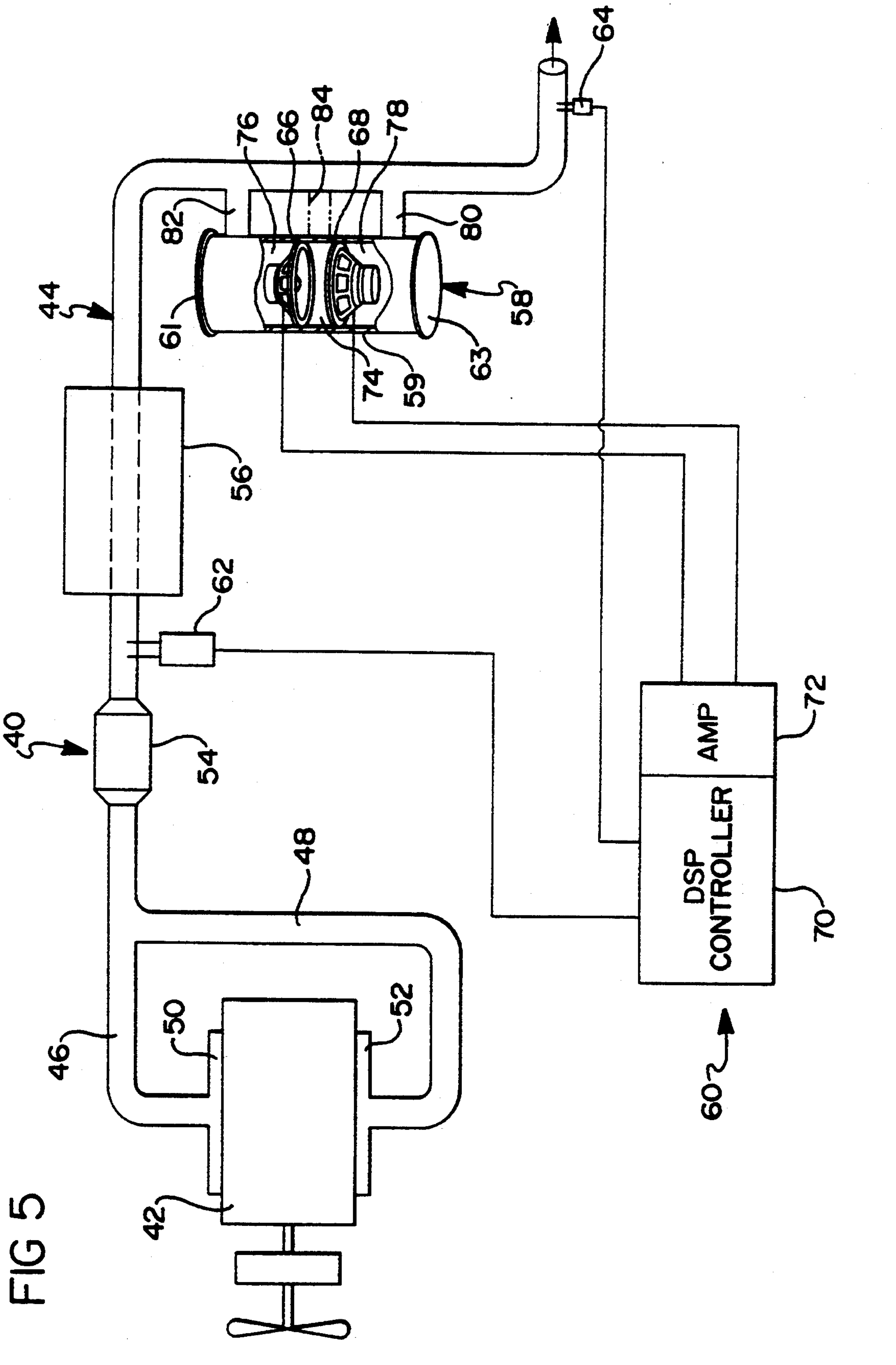
FIG. 5 is a diagrammatic view of an active attenuation system according to the present invention modified to include vibration compensation.

Referring first to FIG. 1, a known noise cancellation system is diagrammatically illustrated to include a microphone 12 exposed to a sound pressure pulse train delivered from a source through a conduit 14. The electrical signal generated by the transducer 12 in response to the sound pressure pulses is fed into electronic control 16 which in turn drives a transducer 18 such as a loudspeaker. As is well known, the control 16 drives the transducer 18 so that the sound pressure is generated by the front of the speaker and introduced to the conduit 14. The emission occurs at a point at which the pulses emitted from the transducer 18 are 180° out of phase with the sound pressure pulses passing through the conduit 14 at that point.

Although there have been many improvements to the system shown in FIG. 1, the improvements do not relate to the transducer efficiency or space saving advantages for the conduit through which the sound pressure pulses travel. Rather, the previously known improvements to the control 16, for example, enabling it to react to changing characteristics of the sound pressure pulses due to changes at the source, or other improvements such as improved positioning or alignment of components to avoid feedback of the signal generated from the transducer 18 which is received at the transducer 12, or error compensation devices which readjust the control 16 in response to the actual degree of cancellation resulting from operation of the transducer 18, show that previous developments exhibit a substantially different emphasis for development of the systems. Notably, all the known prior art examples employ a single face of the transducer diaphragm to produce cancellation pulses.

As shown in FIG. 2, the present invention makes use of the fact that the loudspeaker diaphragm has a front face, diagrammatically indicated at 20, and a rear face, diagrammatically indicated at 22. As a result, each movement of the diaphragm includes a pulse in the front side 20 which is 180° out of phase with the pulse generated at the rear side 22.

While the front face 20 is aimed toward the conduit 14, the rear face 22 is enclosed within a chamber 24 and communicating with a port 26 also aimed toward the conduit 14. As shown in FIG. 4, communication of the pulses transmitted from the back face 22 of the transducer 18 to the chamber 24 and the conduit 26 improves the low end response by expanding the low end of the frequency band. In addition, as shown by Line B in FIG. 4, the efficiency of the transducer at the low end improves significantly. The resonant frequency F, at which improved efficiency occurs, is proportional to $(L2\cdot V2)^{\frac{1}{2}}$.

More dramatic results are recognized when both the front and rear sides of the transducer are coupled through ported chambers as shown in FIG. 3. Chamber 24 enclosing the back side 22 of the transducer 18 has a volume V2 and a port 26 with a length L2. Front side 20 of the transducer 18 is enclosed within the chamber 28 having a volume V1 with a port of length L1. The outlets of the ports 30 and 26 communicate at spaced apart positions along the conduit 14 separated by a distance L3.

As demonstrated in FIG. 4 by plotted line C, such an arrangement provides substantially double the efficiency of a standard transducer noise cancellation setup as represented at plotted line A. Moreover, the frequency band throughout which the increased efficiency occurs is extended at the lower end and cut off at an upper end F2. The high cutoff frequency F2 is proportional to the $(V1\cdot L1)\text{-}\frac{1}{2}$. For the purposes of motor vehicle engine exhaust, a conventional internal combustion engine exhaust valve would generate a maximum frequency of about 250 hertz.

Similarly, the lowest frequency F1 would be proportional to the $V2\cdot L2)\text{-}\frac{1}{2}$. Typically, it will be determined as a convenient idle speed for the motor vehicle engine. As a result, volumes V1 and V2 of the chambers 28 and 24, respectively, as well as the lengths L1 and L2 of the ports 30 and 26, respectively, will be determined as necessary to provide increased efficiency throughout the frequency band in which the sound pressure pulses are passed through the exhaust conduit 14.

The best performance of such a system will occur where the length L3 is substantially less than the wavelength of the highest frequency F2 to be encountered during motor vehicle operation. In addition, L2 should be substantially less than the half wavelength of the highest frequency F2.

While the above discussion shows the advantages of tuning the sound pressure pulses from the rear side of the speaker transducer as well as the front side of the speaker transducer, it is also to be understood as within the scope of the present invention to modify the placement of the ports so that only a single port is in direct communication with the exhaust conduit while the other port communicates between separated chambers within the enclosure. Although such a structure limits direct communication between the hot exhaust gases and the transducer components, it still permits improved efficiency of the transducer operation over the frequency range of the cancellation signal when the chambers and ports are tuned at or near the high and low ends of the bandwidth. Such tuning is consistent with the relationship that frequency is proportional to the $(L\cdot V)^{-\frac{1}{2}}$ for a given port area, as discussed in the description of previous embodiments.

As a result of the tuning provided by the ported chambers of the transducer mounting arrangement of the present invention, the efficiency of the transducer is substantially increased. As a result, the size of the transducer and the energy required to operate the transducer can be substantially reduced over required transducers in previously known noise cancellation systems. In particular, the reduction of energy input requirements substantially reduces the need for power amplification components which are typically the most expensive portions of the electronic control 16. Moreover, the limited space available for packaging such components in a motor vehicle does not prevent the application of an active noise attenuation system in motor vehicles as was expected from previously known noise cancellation systems.

Furthermore, it will be appreciated that any of the previously known improvements employed in noise cancellation systems may be more easily incorporated in limited spaces. For example, where multiple transducers must be used in order to cancel out feedback pulses or to directionalize the cancellation pulses, the power requirements for driving the transducers can be substantially reduced. Moreover, the housing defining the chambers can be used to reduce the effect of heat and other environmental conditions which reduce the useful life of the transducer or other components of the noise cancellation system.

Referring now to FIG. 5, an exhaust system 40 for a motor vehicle engine 42 includes exhaust conduit 44 coupled to header pipes 46 and 48 communicating with the exhaust manifolds 50 and 52, respectively. As used in describing the preferred embodiment, the conduit 44 refers generally to the path communicating with the headers 46 and 48 regardless of the individual components forming the passageway through which the exhaust gases pass. For example, the catalytic converter 54 and the muffler accessory 56 form part of the conduit 44, while active noise cancellation transducer housing 58 shown for the preferred embodiment communicates with the conduit 44. Nevertheless, the housing 58 could also be constructed to support or form part of the conduit 44. The catalytic converter 54 and the passive muffler accessory 56 may be of conventional construction for such items and need not De limited to a particular conventional construction. For example, simple noise damping insulation can be carried in a closed container to reduce vibrations in susceptible portions of the conduit, to combine the passive muffler accessory 56 with an active noise cancellation system.

In addition, the exhaust system 40 includes active noise cancellation controller 60 cooperating with a sensor 62 and feedback sensor 64 as well as the transducers 66 and 68 carried by the transducer housing 58. The electronic control 60 includes a digital signal processing (DSP) controller 70 generating a signal responsive to the signal representative of detected noise in order to generate an out-of-phase cancellation signal. In addition, the controller 40 includes an amplifier circuit 72 that provides sufficient amplitude to the drive signal for the transducers 66 and 68 to match the level of pressure pulses passing the locations at which the transducers 66 and 68 communicate with the conduit 44.

In the preferred embodiment, the housing 58 includes a cylindrical wall 59 and enclosing end walls 61 and 63. The cylindrical wall peripherally engages the transducers 66 and 68 at the interface between the front and rear sides of each transducer. As shown in FIG. 5, the transducers 66 and 68 preferably face each other in coaxial alignment so that the front sides of each transducer communicate with the same chamber 74. Moreover, the rear side of transducer 66 is separated from its front side and communicates with chamber 76 defined by cylindrical wall 59, end wall 61 and the transducer 66. Similarly, the back side of the transducer 68 is separated from the front side by mounting to cylindrical wall 59 and communicates with the chamber 78 defined by cylindrical wall 59, end wall 63 and transducer 68. Nevertheless, it is to be understood that the speakers could be supported by other means such as partition walls or the like within an enclosed housing. Furthermore, it will be understood that the transducers could also be aligned in other positions producing similar results. For example, the speakers could face in the same direction but with oppositely wound coils so that the front side of one speaker facing the rear side of the other speaker moves in the opposite direction in the common chamber 74. Accordingly, either front or rear sides of a transducer could complement or counteract a side of the other speaker in common chamber 74.

As also shown in FIG. 5, the chamber 76 communicates through a port 82 with the exhaust conduit 44 while the chamber 78 communicates through a port 80 at a spaced-apart position from the port 82. With such a porting arrangement, the chamber 74 may be closed so that pressure pulses emanating from the front sides of the transducers 66 and 68 will cancel each other out in the central chamber 74. However, in accordance with the preferred embodiment, the present invention uses a port 84 for coupling chamber 74 in communication with the exhaust conduit 44. Furthermore, it is preferable to tune the chamber 74 and port 84 at or near the highest frequency of the cancellation signal bandwidth. Since the resonant frequency is proportional to $(L\cdot V)^{\frac{1}{2}}$ for a given tuning duct area as previously discussed, proper dimensioning of the chamber and the port enables the signals emanating from the front sides of the transducers 66 and 68 to demonstrate improved transducer efficiency in a predetermined range, preferably the range at or near the highest cutoff frequency in the cancellation signal bandwidth. In addition, the ports 80 and 82 are preferably symmetrically tuned at a frequency at or near the lowest cutoff frequency in the cancellation signal bandwidth. Such tuning eliminates the need for the more powerful electronics required in the amplifier 72.

In any event, the equal and opposite reactions of the diaphragms in transducers 66 and 68 eliminates the substantial vibration of the housing 58 induced by operation of a single transducer. The equal but opposite displacement of the transducer diaphragm faces avoids unopposed vibration of the housing walls forming the housing 58, and limits the associated audible noise, displacement and physical forces which would be generated as a result of transducer diaphragm displacements transferred to the housing in which it is mounted.

Having thus described the present invention, many modifications thereto will become apparent to those skilled in the art to which it pertains without departing from the scope and spirit of the present invention as defined in the appended claims.

I claim:

1. An active, noise cancellation apparatus for cancellation of a noise signal in an interior of a conduit comprising:

a sensor for generating a sensor signal representative of an input pulse train;

a first transducer having a front side and a rear side;

a second transducer having a front side and a rear side;

means for mounting said transducers adjacent to said conduit; and at least one first side of said front and rear sides of said first transducer facing a complement one of said front and rear sides of said second transducer;

electronic control means for driving said transducers in response to said sensor signal and producing an output pulse train having a phase opposite to said input pulse train at a predetermined point;

means for acoustically separating said front side of each transducer from said rear side of the respective transducer, and acoustically coupling at least one of said front and said rear sides of each said transducer with said conduit;

said means for acoustically separating and coupling comprises a housing defining a common chamber enclosing one of said front and rear sides of said first transducer and one of said front and rear sides of second transducer; and further comprising a port for acoustic communication between said chamber and the conduit interior.

2. The invention as described in claim 1 wherein said means for acoustically separating and coupling comprises said housing having two second chambers, one of said second chambers enclosing the other of said front and rear sides of said first transducer, and the other of said second chambers enclosing the other of said front and rear sides of said second transducer, and further comprising a port for acoustic communication between each said second chamber and the conduit.

3. The invention as described in claim 1 wherein said housing comprises means for aligning said first and second transducers on a common axis.

4. The invention as described in claim 3 wherein said output pulse train is coupled to drive said one side of said first transducer and said one side of said second transducer simultaneously in opposite spatial directions.

5. The invention as defined in claim 1 wherein said first and second transducers are aligned on a common axis.

6. The invention as described in claim 4 wherein housing is cylindrical.

7. An active muffler for a motor vehicle exhaust conduit comprising:

a sensor for generating a sensor signal representative of pressure pulses in the conduit;

at least one first transducer positioned for inducing pressure pulses in the conduit at at least a first location along said conduit;

at least one second transducer positioned for inducing pressure pulses in the conduit at at least a second location along said conduit;

electronic control means for driving said first and second transducers to produce cancellation signals of opposite phase to said sensor signal at each said first and second locations;

wherein each said transducer has a first side and an opposite second side generating sound of opposite phase from said first side; and means for acoustically separating said first side from said second side of each respective transducer, and acoustically coupling at least one of said first and second sides of each said transducer to the conduit at each said at least one location, and housing means for aligning said transducers so that at least one of said first and second sides of a said first transducer faces one of said front and rear sides of a said second transducer on a common axis in a common chamber.

8. The invention as described in claim 7 wherein said electronic control means comprises means for driving said at least one side of said first transducer and said one side of said second transducer simultaneously in opposite spatial directions.

9. An active muffler transducer arrangement for a motor vehicle exhaust conduit, comprising:

a first transducer having front and rear sides;

a second transducer having front and rear sides and aligned coaxially with said first transducer;

a housing enclosing both said first and second transducers, and having means for separating said front side of each transducer from said rear side whereby a first of said front and rear sides of said first transducer is isolated from a first of said front and rear sides of said second transducer; and wherein said housing includes at least one first port coupling each of said first sides to the conduit and at least one second port coupling a second of said front and rear sides of said first and second transducers to the conduit.

10. The invention as described in claim 9 wherein said second sides are complementary to move in opposite spatial directions.

* * * * *